United States Patent [19]

Romine

[11] 4,014,803
[45] Mar. 29, 1977

[54] LUBRICANT ADDITIVE
[75] Inventor: Hugh E. Romine, Ponca City, Okla.
[73] Assignee: Continental Oil Company, Ponca City, Okla.
[22] Filed: Aug. 25, 1975
[21] Appl. No.: 607,158

Related U.S. Application Data
[63] Continuation-in-part of Ser. No. 484,024, June 28, 1974, abandoned.

[52] U.S. Cl. .................. 252/32.7 R; 260/326.5 A; 252/56 D
[51] Int. Cl.² ......................................... C10M 3/42
[58] Field of Search .......... 260/326.5 A; 252/56 D, 252/32.7 R

[56] References Cited
UNITED STATES PATENTS
3,235,497  2/1966  Lee ............................. 260/326.5 A

*Primary Examiner*—Lewis Gotts
*Assistant Examiner*—Cary Owens
*Attorney, Agent, or Firm*—Bayless E. Rutherford, Jr.

[57] ABSTRACT

Novel compounds, which are useful as additives in lubricating oils, are disclosed. The novel compounds are represented by the formula

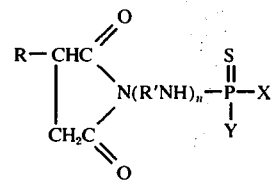

wherein R is an alkenyl group containing 10 to 100 carbon atoms; R' is an alkylene group containing 1 to 5 carbon atoms; $n$ is an integer of 1 to 4; X is selected from the group consisting of $NH_2$, $NR''R''$, $NHR''$, and $OR''$; and Y is selected from the group consisting of $NR''R''$, $NHR''$, $OR''$, and halogen, wherein R'' is alkyl, phenyl, alkyl-substituted phenyl, or alkylene polyamino. A process for preparing the novel compounds is disclosed, also.

22 Claims, No Drawings

LUBRICANT ADDITIVE

CROSS-REFERENCE TO RELATED APPLICATIONS

The present application is a continuation-in-part of Ser. No. 484,024, filed June 28, 1974 now abandoned.

Application Ser. No. 498,345, filed Aug. 19, 1974, now U.S. Pat. No. 3,954,798 and having the same inventor as the present application, is directed to an alternative method of preparing the novel compounds of the present invention.

FIELD OF THE INVENTION AND BACKGROUND

1. Field of the Invention

The invention is in the general field of materials which are suitable for use as additives in lubricating oils. In particular, the invention is in the field of materials which provide lubricity, oxidation inhibition, and dispersancy in lubricating oils.

2. Background

Various materials have been used in lubricating oils for many years. These materials have been used in lubricating oils for many years. These materials known as "lube additives" serve a variety of functions. For example, compounds containing phosphorus, sulfur, or chlorine and combinations thereof have been used as lubricity agents. This type of material serves to improve the load-carrying property of the lubricant. Other materials, such as zinc thiophosphates, phenols, and aryl amines, are known which improve the oxidation stability of lubricants. Still further, other materials have been used to impart a dispersancy property to lubricants. These materials serve to disperse wear products and other foreign materials in the lubricant.

For many years various types of oil-soluble sulfonates have been used as dispersants in lubricants. The preferred oil-soluble sulfonates have been the barium and calcium sulfonates. More recently, an interest has developed in the use of dispersants which do not contain any metal. This latter type of dispersant is referred to as an "ashless dispersant." A particularly preferred type of ashless dispersant contains the polyalkyleneamine moiety. Unfortunately, this type of material is inherently unstable to oxidation.

I have discovered certain novel compounds which, when used in lubricating oils, impart lubricity, oxidation inhibition, and dispersancy to the lubricating oils.

3. Prior Art

An IFI-Plenum computer search failed to produce a reference disclosing the novel compounds of my invention. Also, a search by a Washington searcher failed to produce a reference disclosing the novel compounds of my invention or the process of preparing them. For the record, the Washington searcher did call attention to the following patents which are of general interest: U.S. Pat. Nos. 2,552,574; 3,244,586; 3,286,002; 2,411,527; 2,615,037; 2,865,948; and 3,733,379.

BRIEF SUMMARY OF THE INVENTION

In its broadest aspect, the present invention is directed to compounds which are represented by the formula

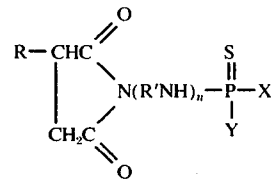

wherein
R is an alkenyl group containing about 10 to about 100, more suitably about 20 to about 75, and preferably, about 12 to about 50, carbon atoms,
R' is an alkylene group containing 1 to 5 carbon atoms,
n is an integer of 1 to 4,
X is selected from the group consisting of NH$_2$, NHR'', NR''R'', and OR'', and
Y is selected from the group consisting of NHR'', NR''R'', OR'', and halogen, wherein, in X and Y, R'' is alkyl, phenyl, alkyl-substituted phenyl, or alkylene polyamino and the halogen is chlorine or bromine, but preferably is chlorine.

It is to be understood that the invention includes mixtures of compounds having the designated formula.

In another aspect, the present invention is directed to lubricating compositions which contain an effective amount of the compounds, or mixture of compounds, described in the foregoing.

In still another aspect, the present invention is directed to a process of preparing the compounds described in the foregoing, wherein the process comprises:

a. reacting a polyalkenylsuccinimide with a phosphoramidodichloridothioate, and b. treating the reaction product of step (a) with a basic material to give the desired product.

The polyalkenylsuccinimide preferably is formed by reacting an alkenyl succinic anhydride with an alkylene polyamine.

The phosphoramidodichloridothioate preferably is prepared by the reaction of thiophosphoryl chloride with an alkylamine.

DETAILED DESCRIPTION

The Compounds

As stated previously the compounds of my invention are represented by the formula

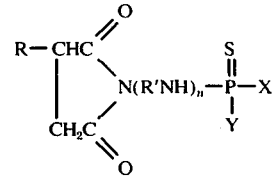

wherein
R is an alkenyl group containing about 10 to about 100, more suitably about 20 to about 75, and preferably, about 12 to about 50, carbon atoms. The alkenyl group normally is obtained by polymerizing by standard means an alkene containing 2 to 5 carbon atoms. Examples of suitable R groups include polyisobutenyl, polybutenyl, polyisopropenyl, polypropenyl, polyisopentenyl, polypentenyl...

The term alkenyl is belived to be well understood by those skilled in the art and is found in numerous patents, e.g., U.S. Pat. Nos. 3,630,903, U.S. 3,185,646, and 3,624,115.

R' is an alkylene group containing 1 to 5, preferably 1 to 2, carbon atoms. Examples of suitable R' groups include methylene, ethylene, propylene, butylene, and amylene.

$n$ is an integer of 1 to 4.

X is selected from the group consisting of $NH_2$, NHR'', NR''R'', and OR'', wherein R'' is a $C_1$-$C_{16}$, preferably $C_2$-$C_5$, alkyl group, phenyl, mono-, or dialkyl substituted phenyl, wherein the alkyl group contains 1 to 16, preferably 1 to 5, carbon atoms or alkylene polyamino containing 1 to 20 carbon atoms. Specific examples of X substituents include dimethyl amino, methylethyl amino, ethylhexylamino, didecylamino, N,N ethyl ethylbenzene amino, N,N butyl propylbenzene amino, N,N butyl diethylbenzene amino, monoethylamino, monobutylamino, monodecylamino, monohexadecylamino, monophenylamino, monobutylphenylamino, ethoxy, butoxy, hexoxy, dodecoxy, and hexadecoxy.

The term alkylene polyamino is believed to be well understood in the art. At times the term is used interchangeably with "polyalkylene polyamine." In order to define the term more specifically, as used herein it refers to materials represented by the formula

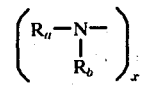

wherein $R_b$ is hydrogen or a $C_1$-$C_3$ alkyl group, $R_a$ is an alkylene group containing 1 to 8 carbon atoms, and $x$ is an integer in the range of 1 to 10. As stated in the foregoing, the alkylene polyamino group contains a total of 1 to 20 carbon atoms.

Y is selected from the group consisting of NHR'', NR''R'', OR'', and halogen, wherein R'' is as defined for X. More suitably, the halogen is chlorine or bromine, but preferably is chlorine. Specific examples of suitable Y substituents, in addition to chloride and bromide, include those given in connection for X for NHR'' and NR''R'' groups.

Usually, the compounds of my invention are a mixture wherein at least a portion of the Y substituents are halogen.

Typical examples of compounds of my invention are the following, wherein in the formula R, R', $n$, X, and Y are as follows:

| R | R' | n | X | Y |
|---|---|---|---|---|
| polyisobutenyl | (1) methylene | 1 | N,N-diethyl-amino | chloride |
| polyisobutenyl | (1) methylene | 1 | N,N-diethyl-amino | N,N-diethyl-amino |
| polyisobutenyl | (1) methylene | 4 | N,N-diethyl-amino | N,N-diethyl-amino |
| polyisobutenyl | (1) methylene | 4 | N,N-diethyl-amino | chloride |
| polyisobutenyl | (1) ethylene | 1 | phenyl-amino | phenyl-amino |
| polyisobutenyl | (1) ethylene | 1 | phenyl-amino | chloride |
| polyisobutenyl | (1) ethylene | 2 | phenyl-amino | chloride |
| polyisobutenyl | (1) ethylene | 2 | phenyl-amino | N-propyl-amino |
| polyisobutenyl | (1) ethylene | 2 | n-hexadecyl-amino | n-propyl-amino |
| polyisobutenyl | (1) ethylene | 3 | N,N-diethyl-amino | N,N-diethyl-amino |
| polyisobutenyl | (2) ethylene | 3 | N,N-diethyl-amino | chloride |
| polyisobutenyl | (2) ethylene | 3 | t-butyl-amino | chloride |
| polyisobutenyl | (2) ethylene | 3 | t-butyl-amino | t-butyl-amino |
| polyisobutenyl | (2) ethylene | 3 | n-propyl-amino | n-propyl-amino |
| polyisobutenyl | (2) ethylene | 3 | n-propyl-amino | chloride |
| polyisobutenyl | (2) ethylene | 3 | phenyl-amino | n-propyl-amino |
| polyisobutenyl | (2) ethylene | 4 | N,N-diethyl-amino | N,N-diethyl-amino |
| polyisobutenyl | (3) ethylene | 4 | N,N-diethyl-amino | chloride |
| polyisobutenyl | (3) ethylene | 4 | t-butyl-amino | chloride |
| polyisobutenyl | (3) ethylene | 4 | t-butyl-amino | t-butyl amino |
| polyisobutenyl | (3) ethylene | 4 | n-propyl-amino | n-propyl-amino |
| polyisobutenyl | (3) ethylene | 4 | n-propyl-amino | chloride |
| polyisobutenyl | (3) ethylene | 4 | phenyl-amino | n-propyl amino |
| polyisobutenyl | (3) propylene | 2 | N,N-diethyl-amino | N,N-diethyl-amino |
| polyisobutenyl | (3) propylene | 2 | N,N-diethyl-amino | chloride |
| polyisobutenyl | (3) propylene | 2 | t-butyl-amino | chloride |
| polyisobutenyl | (4) propylene | 2 | t-butyl-amino | t-butyl-amino |
| polyisobutenyl | (4) propylene | 2 | n-propyl-amino | n-propyl-amino |

-continued

| R | R' | n | X | Y |
|---|---|---|---|---|
| polyisobutenyl | (4) propylene | 2 | n-propyl-amino | chloride |
| polyisobutenyl | (4) propylene | 2 | phenyl-amino | n-propyl-amino |
| polyisobutenyl | (4) propylene | 3 | N,N-diethyl-amino | N,N-diethyl-amino |
| polyisobutenyl | (4) propylene | 3 | N,N-diethyl-amino | chloride |
| polyisobutenyl | (4) propylene | 3 | t-butyl-amino | chloride |
| polyisobutenyl | (4) propylene | 3 | t-butyl-amino | t-butyl-amino |
| polyisobutenyl | (4) propylene | 3 | n-propyl-amino | n-propyl-amino |
| polyisobutenyl | (4) propylene | 3 | n-propyl-amino | chloride |
| polyisobutenyl | (4) propylene | 3 | phenyl-amino | n-propyl-amino |
| polyisobutenyl | (1) butylene | 2 | N,N-diethyl-amino | N,N-diethyl-amino |
| polyisobutenyl | (1) butylene | 2 | N,N-diethyl-amino | chloride |
| polyisobutenyl | (1) butylene | 2 | t-butyl-amino | chloride |
| polyisobutenyl | (1) butylene | 2 | t-butyl-amino | t-butyl-amino |
| polyisobutenyl | (2) butylene | 2 | n-propyl-amino | n-propyl-amino |
| polyisobutenyl | (2) butylene | 2 | n-propyl-amino | chloride |
| polyisobutenyl | (2) butylene | 2 | phenyl-amino | n-propyl-amino |
| polyisobutenyl | (2) butylene | 3 | N,N-diethyl-amino | N,N-diethyl-amino |
| polyisobutenyl | (3) butylene | 3 | N,N-diethyl-amino | chloride |
| polyisobutenyl | (3) butylene | 3 | t-butyl-amino | chloride |
| polyisobutenyl | (3) butylene | 3 | t-butyl-amino | t-butyl-amino |
| polyisobutenyl | (3) butylene | 3 | n-propyl-amino | n-propyl-amino |
| polyisobutenyl | (3) butylene | 3 | n-propyl-amino | chloride |
| polyisobutenyl | (3) butylene | 3 | phenyl-amino | n-propyl-amino |
| polyisopropenyl | (1) methylene | 1 | N,N-diethyl-amino | chloride |
| polyisopropenyl | (2) methylene | 4 | N,N-diethyl-amino | chloride |
| polyisopentenyl | (3) ethylene | 1 | N,N-diethyl-amino | chloride |
| polyisopropenyl | (4) ethylene | 2 | phenyl-amino | chloride |
| polyisopropenyl | (1) butylene | 1 | N,N-diethyl-amino | chloride |
| polypropenyl | (1) ethylene | 1 | N,N-diethyl-amino | chloride |
| polypropenyl | (2) butylene | 1 | N,N-diethyl-amino | chloride |
| polyisopentenyl | (1) methylene | 1 | N,N-diethyl-amino | chloride |
| polyisopentenyl | (2) methylene | 4 | N,N-diethyl-amino | chloride |
| polyisopentenyl | (3) ethylene | 2 | phenyl-amino | chloride |
| polyisopentenyl | (4) butylene | 1 | N,N-diethyl-amino | chloride |

(1) containing 60 carbon atoms
(2) containing 30 carbon atoms
(3) containing 40 carbon atoms
(4) containing 50 carbon atoms

LUBRICANTS CONTAINING THE NOVEL COMPOUNDS

The novel compounds of my invention are useful as an additive in lubricating oils. Examples of suitable lubricating oils include: mineral lubricating oils obtained by conventional refining procedures; synthetic lubricating oils such as polymers of propylene, polyoxyalkylenes, and polyoxypropylenes; synthetic oils such as dicarboxylic acid esters and esters of phosphorus; synthetic hydrocarbon lubricating oils such as di-n-alkylbenzenes and oligomers of $C_6$–$C_{14}$ alpha-olefins; vegetable oils such as corn oil, cottonseed oil, and castor oil; animal oils such as lard oil and sperm oil. Mixtures of these materials can also be used as the base lubricating oils.

Of the preceding examples of suitable lubricating oils, the mineral lubricating oils and synthetic lubricating oils are preferred.

Knowing that the novel compounds of my invention are useful as an additive in lubricating oils, any person skilled in the art can readily determine both a suitable and an optimum amount. Suitable amounts of the novel compounds in lubricating oils are in the range of about 0.1 to about 20 weight percent. Preferred amounts are in the range of about 2 to about 10 weight percent.

THE PROCESS

Materials Used

Suitable polyalkenylsuccinimides are represented by the formula $$\begin{array}{c} R-CH-C{\displaystyle \underset{\diagdown}{\overset{\diagup O}{\nearrow}}} \\ | \quad\quad N(R'NH)_nH \\ CH_2-C{\displaystyle \underset{\diagdown O}{\nearrow}} \end{array}$$

wherein R is an alkenyl group of about 10 to about 100, more suitably about 20 to about 75, and preferably about 12 to about 50, carbon atoms, R' is an alkylene group containing 1 to about 5, preferably 1 to 2, carbon atoms, and $n$ is an integer of 1 to 4.

Specific examples of R and R' have been given in the description of the compounds.

Polyalkenylsuccinimides of the type described above are well known and are referred to in numerous patents. Typically, they are prepared by reacting an alkenyl succinic anhydride with an alkylene polyamine.

In addition to thiophosphoryl chloride ($PSCl_3$) any combination of $P_4S_{10}$ and HCl which yields $PSCl_3$ in situ can be used.

Suitable amines to prepare the phosphoramidodichloridothioates are those which yield the radicals $NH_2$, NHR'', NR''R''', and OR'', wherein R'' is as described in connection with the compounds. Primary $C_2-C_6$ aliphatic amines are preferred.

Acceptor—in describing the preparation of the phosphoramidodichloridothioate, the term "acceptor" is used. This term refers to amines of the type described in the foregoing and to inorganic oxides, such as CaO, MgO, etc—in other words, materials which react with HCl.

Preparation of the Phosphoramidodichloridothioate

The reaction for this process can be shown as follows $$PSCl_3 + 2HNR''R''' \longrightarrow \overset{S}{\underset{\parallel}{(Cl)_2PNR''R'''}} + HNR''R''' \cdot HCl \quad (1)$$
(usually insoluble)

or $$PSCl_3 + HNR''R''' + Acceptor \longrightarrow \overset{S}{\underset{\parallel}{(Cl_2)PNR''R'''}} + Acceptor \cdot HCl \quad (2)$$

From the above-described reactions, it is apparent that when the acceptor is an amine, the reaction requires twice as much amine as when a non-amine is the acceptor.

More specifically, the amount of $PSCl_3$ to amine in the reaction can be stated as follows on a molar basis Suitable range: 0.8 to 3.0.
Preferable range: 1 to 2.5.

Theoretically, the reaction does not require the presence of a solvent. However, since the reaction is exothermic, usually a solvent is desirable in order to control reaction temperature. Generally, any solvent is suitable in which the reactants (e.g., $PSCl_3$, etc) are soluble. Preferably, the solvent is one in which, in addition, the amine salts are insoluble. Typical examples of suitable solvents include benzene, toluene, p-dioxane, diethyl ether, bis 2-methoxyethyl ether, and dimethylformamide.

The reaction can be conducted at any convenient temperature below the boiling point of the lowest boiling reactant (or solvent). Generally, the temperature can be in the range of $-80°$ to $110°$ C. Typically, ambient temperatures are employed.

Control of pressure is not required. Any convenient pressure can be used.

Inasmuch as the reaction is exothermic, preferably the amine is added to the $PSCl_3$ incrementally. Typically, the time of addition is 1 to 4 hours in the laboratory. Conceivably, the time of addition could be much longer—e.g., 24–48 hours; however, such is not practical.

Reaction of the Phosphoramidodichloridothioate and Alkenyl Succinimide

The basic reaction can be shown as follows:

$$\begin{array}{c} R-CH-C{\displaystyle \underset{\diagdown}{\overset{\diagup O}{\nearrow}}} \\ | \quad\quad N(R'NH)_nH + (Cl)_2\overset{S}{\underset{\parallel}{P}}NR''R''' \longrightarrow \\ CH_2-C{\displaystyle \underset{\diagdown O}{\nearrow}} \end{array}$$

$$\begin{array}{c} RCHC{\displaystyle \underset{\diagdown}{\overset{\diagup O}{\nearrow}}} \\ | \quad\quad N(R'NH)_n-\overset{S}{\underset{\parallel}{P}}(Cl)NR''R''' \cdot HCl \\ CH_2-C{\displaystyle \underset{\diagdown O}{\nearrow}} \end{array}$$

The preferable amount of materials is the stoichiometric, i.e., 1:1. However, other ratios can be employed in the ratio of 10:1 to 0.1:1.

While not absolutely necessary, usually the reaction is conducted in the presence of a solvent which serves to reduce the viscosity of the admixture. Any material capable of dissolving both the reactants and the product is suitable as a solvent. Typical examples of suitable solvents include aromatic hydrocarbons such as benzene and toluene.

The reaction can be conducted at any convenient temperature from ambient up to the boiling point of the solvent. Generally, a suitable temperature is in the range of about $50°$ to about $130°$ C.

Control of pressure is not required. Any convenient pressure can be used.

The reaction time is not critical and can be determined by any person skilled in the art. Typically, the reaction time is in the range of about 1 to about 24 hours.

Treatment of the Reaction Product of the Phosphoramidodichloridothioate and Alkenyl Succinimide With a Basic Compound As indicated in the equation showing the basic reaction, the initial reaction product contains residual chlorine. The properties of the final product as a lube oil additive are affected by the presence of the residual chlorine. Generally, it is preferred to remove all active chlorine. However, the presence of bound chlorine may be desirable.

The reaction product is treated with a basic material (or a hydrogen chloride acceptor) to effect reduction of the chloride content. Examples of suitable basic materials (or hydrogen chloride acceptors) include metal oxides (e.g., CaO), amines (ammonia, primary, secondary, or tertiary), and metal alkoxides (e.g., sodium methoxide).

Knowing that the reaction product is to be treated with a basic material, any person skilled in the art can readily determine the exact details. Typically, the treatment is conducted by adding the basic material to the reaction product and maintaining a temperature of about 50° to about 150° C for a time in the range of ½ to 24 hours. The amount of basic material usually is at least one equivalent per mole of phosphoramidodichloridothioate used to prepare the crude reaction product. The reaction admixture is then cooled to room temperature, filtered to remove suspended salts, and distilled to remove excess basic material (if liquid) and any solvent present.

In order to disclose the nature of the present invention still more clearly, the following examples will be given. It is to be understood that the invention is not to be limited to the specific conditions or details set forth in these examples except insofar as such limitations are specified in the appended claims.

EXAMPLE 1

This example shows the reaction of thiophosphoryl chloride with n-propylamine.

A 500-ml flask equipped with a thermometer, an addition funnel, and a stirrer was charged with 17.0 g (0.1 m) of $PSCl_3$ dissolved in 50 ml of p-dioxane. A solution of 11.8 g (0.2 m) of $n\text{-}PrNH_2$ in 50 ml of p-dioxane was added dropwise during 40 minutes. The temperature rose to 42° C, and some darkening occurred. The mixture was quenched, water washed, and dried ($Na_2SO_4$) to give a tan oil product. This was identified as 90 percent N-n-propyl phosphoramidodichloridothioate: mass spectrum molecular ion peaks at m/c 191, 193, and 195.

Analysis: Calculated for $C_3H_8NPSCl_2$: C, 18.8; H, 4.2; N, 7.3. Found: C, 16.36; H, 5.65; N, 7.42.

EXAMPLE 2

This example shows the reaction of polyisobutenylsuccinimide with the n-propyl phosphoramidodichloridothioate of Example 1.

A 2 l flask equipped with an addition funnel, a thermometer, a stirrer, and a reflux condenser with take-off was charged with 377 g (0.20 eq) of polyisobutenylsuccinic anhydride and 200 ml of toluene. During 40 minutes 37.8 g (0.2 m) of $NH_2(CH_2CH_2NH)_4H$ was added, with a mild exothermic reaction resulting. Nine hours of slow refluxing gave 5.0 ml of azeotroped water and a bright amber succinimide product. During 30 minutes 76.4 g (0.4 m) of n-propyl phosphoramidodichloridothioate was added to the cooled succinimide. An 11° C temperature increase was noted. The mixture was stirred at 50° C 1 hour and cooled to 30° C prior to the addition of 24.0 g (0.40 m) of $NH_2CH_2CH_2NH_2$. Slight haziness developed along with a 15° C temperature kick during the 30-minute addition.

The crude product was divided into two equal portions, which were treated in Examples 3 and 4.

EXAMPLE 3

Portion A of the crude product of Example 2 was admixed with 40.0 g (0.40 mole) of triethylamine and stirred at 50° C for 1 hour. It was then heated briefly to reflux, cooled, and centrifuged to remove solids. After removal of solvents by distillation, 179 g of bright, amber fluid product was obtained. The product was designated A.

Analysis: Calculated from combining weights: N, 6.38; P, 2.57; S, 2.65. Found: N, 4.61; P, 1.70; S, 1.45; Cl, 1.26 (all weight percent).

EXAMPLE 4

Portion B of the crude product of Example 2 was combined with 25.0 g (0.45 m) of CaO and refluxed at 110° C for 1 hour. The product was centrifuged and stripped of solvent to give 148 g of a hazy, amber fluid product. The product was designated B. Analysis: Calculated from combining weights: N, 6.38; P, 2.57; S, 2.65. Found: N, 4.06; P, 1.57; S, 1.41; Cl, 1.21 (all weight percent).

EXAMPLE 5

This example shows the preparation of another crude reaction product of polyisobutenylsuccinimide with n-propylphosphoramidodichloridothioate.

The procedure of Example 2 was used.

413 g (0.30 eq) of polyisobutenylsuccinic anhydride was reacted with 57.0 g (0.30 m) of tetraethylenepentamine. The product was then reacted with 37.8 g (0.20 m) of n-propyl phosphoramidodichloridothioate (as in Example 1). The crude reaction product was then treated in Examples 6, 7, and 8.

EXAMPLE 6

To two-thirds of the crude reaction product of Example 5 there was added 12.0 g (0.2 m) of ethylene diamine. A 3° C temperature rise occurred with no visible solids formation. The admixture was heated briefly to reflux temperature (110° C) which resulted in some solids formation. One-half of this treated product was centrifuged and stripped of solvent to give 86.2 g of a dark, viscous product.

The product was designated C.

Analysis: Calculated from combining weights: N, 5.87; P, 1.22; S, 1.27. Found: N, 4.9; P, 0.52; S, 1.0; Cl, 0.44 (all weight percent).

EXAMPLE 7

The remaining one-half of the ethylene diamine treated product of Example 6 was combined with 25.0 g of triethylamine, and the admixture was refluxed for 15 minutes. After cooling, the admixture was centrifuged and stripped of solvent to give 114.6 g of a dark oil product.

The product was designated D.

Analysis: Calculated from combining weights: N, 5.87; P, 1.22; S, 1.27. Found: N, 4.7; P, 0.79; S, 1.2; Cl, 0.43 (all weight percent).

EXAMPLE 8

The remaining one-third of the crude product of Example 5 was placed in a 1-liter flask equipped with bubbler, a stirrer, a dry ice condenser, and an ammonia absorber. Ammonia gas was bubbled through the crude product for 1 hour at a rate of 50 cc per minute, which resulted in a slight warming and salt formation.

The ammonia-treated product was cooled, centrifuged, and stripped of solvent to give 115.7 g of a dark, oil product.

The product was designated E.

Analysis: Calculated from combining weights: N, 5.87; P, 1.22; S, 1.27. Found: N, 3.9; P, 0.70; S, 0.7; Cl, 0.47 (all weight percent).

In order to demonstrate that Products A, B, C, D, and E have utility as a lubricating additive, a series of bench tests were run on a base oil containing the various products. The base oil was a solvent refined pale oil having a viscosity of 170 SSU at 100° F. An amount of additive was added to the base oil to provide 0.5 percent by weight phosphorus in the compounded lubricant. In order to provide a basis for comparison, a commercial motor oil additive package meeting SE-30 specifications was added to this same base oil and also run. It should be noted that the comparative motor oil contained 0.14 weight percent phosphorus.

Federal Test Method 5308.6, modified to run at 300° F for 72 hours, was used to evaluate antioxidant, corrosion, and dispersant properties. The sludging tendency of the oil, as measured by amount of sludge, provides a measure of dispersancy. As is known to those skilled in this art, in evaluating results obtained using this method, lower values indicate better results.

The extreme pressure (EP) properties were measured using a MacMillan apparatus. This apparatus, and procedure, operates on the same principle as the Timken and LFW-1 testers with a single stationary block bearing against a rotating ring. Single line contact is achieved in the particular equipment used, which has been modified to accommodate LFW-1 test elements. Dead weight arm lever loading is employed.

Wear is determined by measuring the width of the scar after various times with a predetermined load and speed. Load carrying ability (i.e., maximum film strength) is measured by step loading until failure is indicated by seizure or a sharp increase in scar width.

The MacMillan tester can operate at several speeds. However, the tests reported herein were conducted at 400 feet per minute. Loading is from 0 to 11 pounds, corresponding to Hertz pressures up to about 65,400 psi. The tests were conducted at an oil reservoir temperature of 130° F.

With regard to the results obtained, for film strength a higher value indicates better results. For wear scar, lower results are better and with less change for a constant time.

The results of the bench tests are shown in Table I.

TABLE I

|  | PRODUCT NUMBER | | | | | Commercial Motor Oil |
|---|---|---|---|---|---|---|
|  | A | B | C | D | E | |
| Wt % Additive | 2.9 | 3.2 | 9.6 | 6.3 | 7.1 | — |
| Wt % Blend Phos. | 0.05 | 0.05 | 0.05 | 0.05 | 0.05 | 0.14 |
| Test Results | | | | | | |
| MacMillan E. P. | | | | | | |
| Max. Non-Seizure | | | | | | |
| Load (Lbs) | 2 | 4 | 4 | 3 | 2 | 4 |
| Film Strength (psi) | 5,300 | 12,000 | 11,100 | 8,600 | 5,300 | 6,000 |
| MacMillan Antiwear | | | | | | |
| Wear Scar, 10 Min., 2# | 0.90 | 0.60 | 0.70 | 0.80 | 0.90 | 1.10 |
| (mm):   25 Min., 2# | 0.90 | 0.60 | 0.75 | 0.95 | 0.95 | 1.10 |
| 50 Min., 2# | 1.00 | 0.75 | 0.90 | 0.85 | 1.40 | 1.15 |
| 80 Min., 2# | 1.45 | 0.80 | 0.90 | 0.80 |  | 1.45 |
| FTM 5308.6 at 300° F, 72 Hr. | | | | | | |
| % Vis. Inc. at 100° F | −.03 | −0.2 | −0.5 | +7.8 | −3.5 | +0.2 |
| Acid No. Change | 0.60 | 0.21 | 3.05 | 1.72 | 1.01 | 0.32 |
| Sludge (mg) | 8 | 5 | 5 | 5 | 18 | 5 |
| Coupon Wt. Chg. (mg) | | | | | | |
| Mg | −0.2 | −0.1 | 0 | −0.2 | 0 | −0.1 |
| Al | 0 | −0.1 | −0.1 | +0.1 | 0 | 0 |
| Cu | +0.2 | −2.2 | −1.9 | −2.1 | −1.6 | −0.5 |
| Fe | −0.3 | −0.3 | −0.4 | −0.3 | −0.3 | −0.2 |
| Ag | +1.8 | −0.6 | +0.5 | +1.4 | +0.2 | −0.4 |

Thus, having described the invention in detail, it will be understood by those skilled in the art that certain variations and modifications can be made without departing from the spirit and scope of the invention as defined herein and in the appended claims.

I claim:

1. Compounds represented by the formula

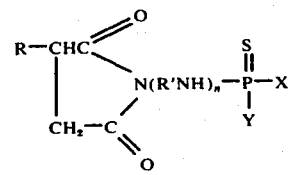

wherein
R is an alkenyl group containing about 10 to about 100 carbon atoms,
R' is an alkylene group containing 1 to about 5 carbon atoms,
n is an integer of 1 to 4,
X is selected from the group consisting of $NH_2$, NHR", NR"R", and OR", wherein R" is a $C_1$-$C_{16}$ alkyl group, phenyl, mono- or dialkyl substituted phenyl, wherein the alkyl group contains 1 to 16 carbon atoms, or alkylene polyamino containing 1 to 20 carbon atoms and being represented by the formula $$\left( \begin{array}{c} R_a-N- \\ | \\ R_b \end{array} \right)_x$$

wherein $R_b$ is hydrogen or a $C_1$-$C_3$ alkyl group, $R_a$ is an alkylene group containing 1 to 8 carbon atoms, and $x$ is an integer in the range of 1 to 10, and Y is selected from the group consisting of NHR'', NR''R'', OR'', chloride, and bromide, wherein R'' is as defined for X.

2. The compounds of claim 1 characterized further in that R' is ethylene, and $n$ is 4.

3. The compounds of claim 1 characterized further in that R' is methylene, and $n$ is 4.

4. The compounds of claim 2 characterized further in that X is represented by the formula NHR'' or the formula NR''R'', wherein R'' is an alkyl group containing 2 to 5 carbon atoms.

5. The compounds of claim 4 characterized further in that Y is represented by the formula NHR'' or the formula NR''R'', wherein R'' is an alkyl group containing 2 to 5 carbon atoms.

6. The compounds of claim 4 characterized further in that Y is chloride ion.

7. The compounds of claim 6 wherein R is an alkenyl group containing about 20 to about 75 carbon atoms.

8. A lubricating oil composition comprising a major amount of a mineral or synthetic base lubricating oil and an effective amount in the range of from about 0.1 to about 20 weight percent of compounds represented by the formula $$\begin{array}{c} R-CHC\diagup^O \\ | \quad\quad\diagdown \\ \quad\quad\quad N(R'NH)_n-\overset{S}{\underset{|}{P}}-X \\ CH_2-C\diagup \quad\quad Y \\ \diagdown_O \end{array}$$

wherein

R is an alkenyl group containing about 10 to about 100 carbon atoms,

R' is an alkylene group containing 1 to about 5 carbon atoms, $n$ is an integer of 1 to 4, X is selected from the group consisting of $NH_2$, NHR'', NR''R'', and OR'', wherein R'' is a $C_1$–$C_{16}$ alkyl group, phenyl, mono- or dialkyl substituted phenyl, wherein the alkyl group contains 1 to 16 carbon atoms, or alkylene polyamino containing 1 to 20 carbon atoms and being represented by the formula $$\left( \begin{array}{c} R_a-N- \\ | \\ R_b \end{array} \right)_x$$

wherein $R_b$ is hydrogen or a $C_1$-$C_3$ alkyl group, $R_a$ is an alkylene group containing 1 to 8 carbon atoms, and $x$ is an integer in the range of 1 to 10, and Y is selected from the group consisting of NHR'', NR''R'', OR'', chloride, and bromide, wherein R'' is as defined for X.

9. The lubricating oil composition of claim 8 wherein the compounds are characterized further in that R' is ethylene and $n$ is 4.

10. The lubricating oil composition of claim 8 wherein the compounds are characterized further in that R' is methylene and $n$ is 4.

11. The lubricating oil composition of claim 9 wherein the compounds are characterized further in that X is represented by the formula NHR'' or the formula NR''R'', wherein R'' is an alkyl group containing 2 to 5 carbon atoms.

12. The lubricating oil composition of claim 11 wherein the compounds are characterized further in that Y is represented by the formula NHR'' or the formula NR''R'', wherein R'' is an alkyl group containing 2 to 5 carbon atoms.

13. The lubricating oil composition of claim 11 wherein the compounds are characterized further in that Y is chloride ion.

14. A process for preparing compounds of the type described in claim 1 wherein the process comprises:

a. reacting a polyalkenylsuccinimide with a phosphoramidodichloridothioate, and b. treating the reaction product of step (a) with a basic material selected from the group consisting of metal oxides, amines, and metal alkoxides.

15. The process of claim 14 wherein the polyalkenylsuccinimide is represented by the formula $$\begin{array}{c} R-CH-C\diagup^O \\ | \quad\quad\diagdown \\ \quad\quad\quad N(R'NH)_nH \\ CH_2-C\diagup \\ \diagdown_O \end{array}$$

wherein R is an alkenyl group containing about 10 to about 100 carbon atoms, R' is an alkylene group containing 1 to 5 carbon atoms, and $n$ is an integer of 1 to 4.

16. The process of claim 14 wherein the phosphoramidodichloridothioate is represented by the formula $$(X)_2\overset{S}{\overset{\|}{P}}NR''R''\ \text{or the formula}\ (X)_2\overset{S}{\overset{\|}{P}}NHR''$$

wherein R'' is a $C_1$–$C_{16}$ alkyl group, phenyl, a mono- or dialkyl substituted phenyl, wherein the alkyl group contains 1 to 16 carbon atoms, or alkylene polyamino containing 1 to 20 carbon atoms and being represented by the formula $$\left( \begin{array}{c} R_a-N- \\ | \\ R_b \end{array} \right)_x$$

wherein $R_b$ is hydrogen or a $C_1$–$C_3$ alkyl group, $R_a$ is an alkylene group containing 1 to 8 carbon atoms, and $x$ is an integer in the range of 1 to 10, and wherein X is a chloride or bromide anion.

17. The process of claim 16 wherein R'' is a $C_2$ to $C_5$ alkyl group.

18. The process of claim 16 wherein the polyalkenylsuccinimide is represented by the formula

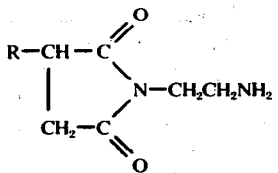

wherein R is as defined in claim 15.

19. The process of claim 17 wherein X is a chloride anion.

20. The process of claim 19 wherein the basic material used in step (b) is a metal oxide, amine or metal alkoxide.

21. The process of claim 14 wherein the amount of polyalkenylsuccinimide to phosphoramidodichloridothioate, on a molar basis, is in the range of 10:1 to 0.1:1.

22. The process of claim 18 wherein the amount of polyalkenylsuccinimide to phosphoramidodichloridothioate, on a molar basis, is in the range of 10:1 to 0.1:1.

* * * * *